(12) United States Patent
Shinoda

(10) Patent No.: US 8,512,639 B2
(45) Date of Patent: Aug. 20, 2013

(54) CHANNEL SUBSTRATE

(75) Inventor: Masataka Shinoda, Tokyo (JP)

(73) Assignee: Sony Corporation, Tokyo (JP)

( * ) Notice: Subject to any disclaimer, the term of this patent is extended or adjusted under 35 U.S.C. 154(b) by 249 days.

(21) Appl. No.: 12/437,130

(22) Filed: May 7, 2009

(65) Prior Publication Data
US 2009/0285720 A1  Nov. 19, 2009

(30) Foreign Application Priority Data

May 14, 2008 (JP) .................................. 2008-127489

(51) Int. Cl.
*G01N 21/01* (2006.01)
(52) U.S. Cl.
USPC .................. 422/82.05; 422/82.08; 422/82.09; 422/68.1
(58) Field of Classification Search
USPC ............... 422/68.1, 82.05, 82.08, 82.09, 502, 422/503
See application file for complete search history.

(56) References Cited

U.S. PATENT DOCUMENTS

| | | | | |
|---|---|---|---|---|
| 6,495,104 B1 * | 12/2002 | Unno et al. | ................... | 422/68.1 |
| 2002/0180963 A1 | 12/2002 | Chien et al. | | |
| 2007/0146704 A1 * | 6/2007 | Schmidt et al. | ............... | 356/338 |
| 2007/0217953 A1 * | 9/2007 | Brennen et al. | ............ | 422/82.05 |
| 2008/0186504 A1 * | 8/2008 | Kiesel et al. | ................... | 356/454 |

FOREIGN PATENT DOCUMENTS

| | | |
|---|---|---|
| DE | 199009692 | 3/2000 |
| DE | 19933458 | 2/2001 |
| EP | 0479231 | 4/1992 |
| EP | 1462805 | 9/2004 |
| EP | 1881318 | 1/2008 |
| JP | 05-045359 | 2/1993 |
| JP | 05-060756 | 3/1993 |
| JP | 2002-516982 | 6/2002 |
| JP | 2007-057378 | 3/2007 |
| JP | 2007-170828 | 7/2007 |

OTHER PUBLICATIONS

European Office Action issued on Sep. 8, 2009, for corresponding European Patent Application 09 00 5666.
Japanese Patent Office, Notification of reasons for refusal issued in connection with Japanese Patent Application No. 2008-127489, dated Aug. 21, 2012. (3 pages).

\* cited by examiner

*Primary Examiner* — In Suk Bullock
*Assistant Examiner* — Paul Hyun
(74) *Attorney, Agent, or Firm* — K&L Gates LLP

(57) ABSTRACT

The present application provides a channel substrate having a channel provided therein and includes a plurality of detection portions configured to detect a specimen in the channel using an optical device, an introducing portion configured to introduce the specimen into the channel, and a discharging portion configured to discharge the specimen from the channel. The detection portions have, on at least one of the opposite faces of the channel substrate, detection portion surfaces which have distances different from each other to the channel.

11 Claims, 15 Drawing Sheets

Prior Art

CHANNEL SUBSTRATE

CROSS REFERENCES TO RELATED APPLICATIONS

The present application claims priority to Japanese Priority Patent Application JP 2008-127489, filed in the Japan Patent Office on May 14, 2008, the entire content of which is hereby incorporated by reference.

BACKGROUND

This present application relates a channel substrate, and more particularly to a channel substrate having a detection portion surface.

In recent years, a technique (μTAS: Micro Total Analysis System) of carrying out various operations for chemical reaction, synthesis, production, analysis and so forth in a fine region making use of micromachining is applied in a wide variety of fields. For example, the μTAS technique can be applied in the following manner. In particular, various kinds of solution, organic fine particles such as cells or microorganisms, fine particles such as micro beads or like elements are circulated in a channel, a capillary or a channel formed on a two- or three-dimensional substrate of a plastic material or a glass material. Then, such elements are measured using physical means or chemical means to carry out analysis, separation or the like of the elements. Or, interaction or reaction between different substances is permitted to proceed in the channel and is measured by physical means or chemical means.

A process which uses the μTAS is advantageous in that an operation can be carried out with a smaller amount of specimen than that by an existing process, that a high-sensitivity process can be carried out in short time and that an operation can be carried out at various places. Therefore, the μTAS has been placed into practical use in a wide variety of fields such as the fields of food, agriculture and optics for diagnosis of a disease, chemical screening of a drug or the like, forensic medicine, exhaustive analysis of genetic information and so forth, functional analysis of an organic substance, analysis of in vivo reaction and so forth.

One of representative measurement principles used in the μTAS technique is measurement by optical means. For example, fluorimetry, diffused light measurement, transmitted light measurement, reflected light measurement, diffracted light measurement, ultraviolet spectrometry, infrared spectrometry, Raman spectrometry, FRET (Fluorescent Resonance Energy Transfer) measurement, FISH (Florescent in Situ Hybridization) measurement and other various fluorescence spectral measurements can be used to carry out measurement of an optical property.

An example of a related art regarding measurement by optical means according to such μTAS technique is described with reference to FIG. 15. A channel along which a specimen is communicated is provided in the inside of a transparent substrate, and the specimen is communicated from a specimen introducing portion to a specimen discharging portion. An excitation ray L1 emitted from a light source D1 is irradiated upon the specimen communicated in a channel 62 in a channel substrate 6 through a condensing lens D2.

As the excitation ray L1 is irradiated upon the specimen, fluorescent light or the like is generated from the specimen. Such fluorescence L2 can be condensed by a condensing lens D3 and measured by a detector D4.

Japanese Patent Laid-Open No. 2007-057378 discloses a microchip which includes a substrate having a translucent property at least at a portion thereof, a fine channel formed in a region of the substrate which includes the translucent portion, a protein fixing portion having very small recesses and projections provided at the translucent portion of the fine channel, and protein fixed at the protein fixing portion for peculiarly reacting with a specimen.

Japanese Patent Laid-Open No. 2007-170828 discloses a substrate for optical test for use with a method of irradiating, in a state wherein a specimen is circulated in a channel provided in the inside of the substrate, light upon the specimen in the channel to detect detection light of a particular wavelength. The substrate for optical test is configured such that fine recesses and projections are provided periodically on an inner wall face of the channel such that the period of the recesses and projections is smaller than 50% of the wavelength of the detection light.

SUMMARY

However, the channel substrate 6 and so forth described above have a problem that measurement of a specimen cannot be carried out suitably using various kinds of optical measuring means The optical measuring means uses a condensing lens whose performance depends upon the type of the optical measuring means. One of indices used to indicate a performance of a condensing lens is the numerical aperture NA. The numerical aperture NA is an index representative of a resolving power of a lens and is given by the following expression (1):

$$NA = n \cdot \sin\theta \quad (1)$$

where n is the refractive index of a medium between the lens and the specimen and θ is the maximum angle of a beam of light introduced from the specimen to the lens with respect to the optical axis of the lens. Since the resolving power of the lens increases in inverse proportion to the numerical aperture NA, as the numerical aperture NA increases, the resolving power of the lens increases.

Thus, since a lens of a large numerical aperture NA exhibits a great maximum angle Θ of a beam of light introduced from the specimen to the lens with respect to the optical axis, the working distance WD representative of the distance from an end of the lens to a focus of the lens is short as can be recognized from FIG. 16. Therefore, in an existing channel substrate wherein the distance from the surface of the substrate to the channel is fixed, a condensing lens which has a large numerical aperture NA and therefore has a short working distance WD cannot be positioned sufficiently near to the channel. Therefore, the existing channel substrate has a problem that measurement of a specimen cannot be carried out favorably.

Therefore, it is desirable to provide a channel substrate with which a specimen in a channel can be measured with a high degree of accuracy irrespective of the type or performance of optical measuring means.

According to an embodiment, there is provided a channel substrate having a channel provided therein, including a plurality of detection portions configured to detect a specimen in the channel using optical means, an introducing portion configured to introduce the specimen into the channel, and a discharging portion configured to discharge the specimen from the channel, the detection portions having, on at least one of the opposite faces of the channel substrate, detection portion surfaces which have distances different from each other to the channel.

In the channel substrate, since the detection portion surfaces of the detection portions have distances different from each other to the channel on at least one of the opposite faces of the channel substrate, a detection portion having a suitable detection portion surface can be selected in response to the performance of the optical measuring means used for measurement. As a result, measurement can be carried out with a higher degree of accuracy using various optical measuring means.

The detection portion surfaces of the detections are not limited particularly only if the distances thereof to the channel are different from each other on at least one of the opposite faces of the channel substrate. However, preferably the detection portion surfaces of the detection portions have distances different from each other to the channel on both of the opposite faces of the channel substrate. In this instance, since the distances to the channel are different from each other on the opposite sides of the channel substrate, a detection portion having a suitable detection portion surface can be selected in response to both of the performance of a condensing lens on the light source side and the performance of a condensing lens on the detector side. Consequently, detection can be carried out with a higher degree of accuracy using the optical means.

The number of introducing portions is not limited particularly, and an additional introducing portion or portions may be connected to the channel. Where such two or more introducing portions are connected to the channel, a plurality of specimens can be introduced into the channel at the same time.

Preferably, the channel substrate further includes an identification shape from which information regarding the channel substrate can be identified. Where the identification shape is provided, wrong use or the like of the channel substrate can be prevented.

In this instance, preferably the identification shape is a cutaway shape. Where the identification shape is a cutaway shape, this can be formed so as to compositely represent information regarding the channel substrate and besides the information can be read using a scanner, a sensor or the like.

Preferably, the channel substrate further includes a positioning shape provided on the channel substrate for defining the position of the channel substrate upon installation of the channel substrate. Where the positioning shape is provided, when various processes are carried out in the channel or upon storage, transportation and so forth of the channel substrate, the channel substrate can be held stably.

Although the position at which the positioning shape is to be provided is not limited particularly, preferably the positioning shape is provided on at least one of the opposite faces of the channel substrate.

Preferably, the positioning shape is provided on both of the upper and lower faces of the channel substrate such that the positioning shape provided on the upper face of the channel substrate is complementary to the positioning shape provided on the lower face of the channel substrate. Where the channel substrate is configured in this manner, when a plurality of such channel substrates are stacked in a vertical direction, the channel substrates are fitted with each other in the vertical direction. Consequently, the channel substrates can be stored or transported stably.

With the channel substrate, measurement of a specimen or the like in the channel can be carried out with a high degree of accuracy irrespective of the type or performance of the optical measuring means.

Additional features and advantages of the present application are described in, and will be apparent from, the following Detailed Description and the figures.

DETAILED DESCRIPTION

Figure 1:
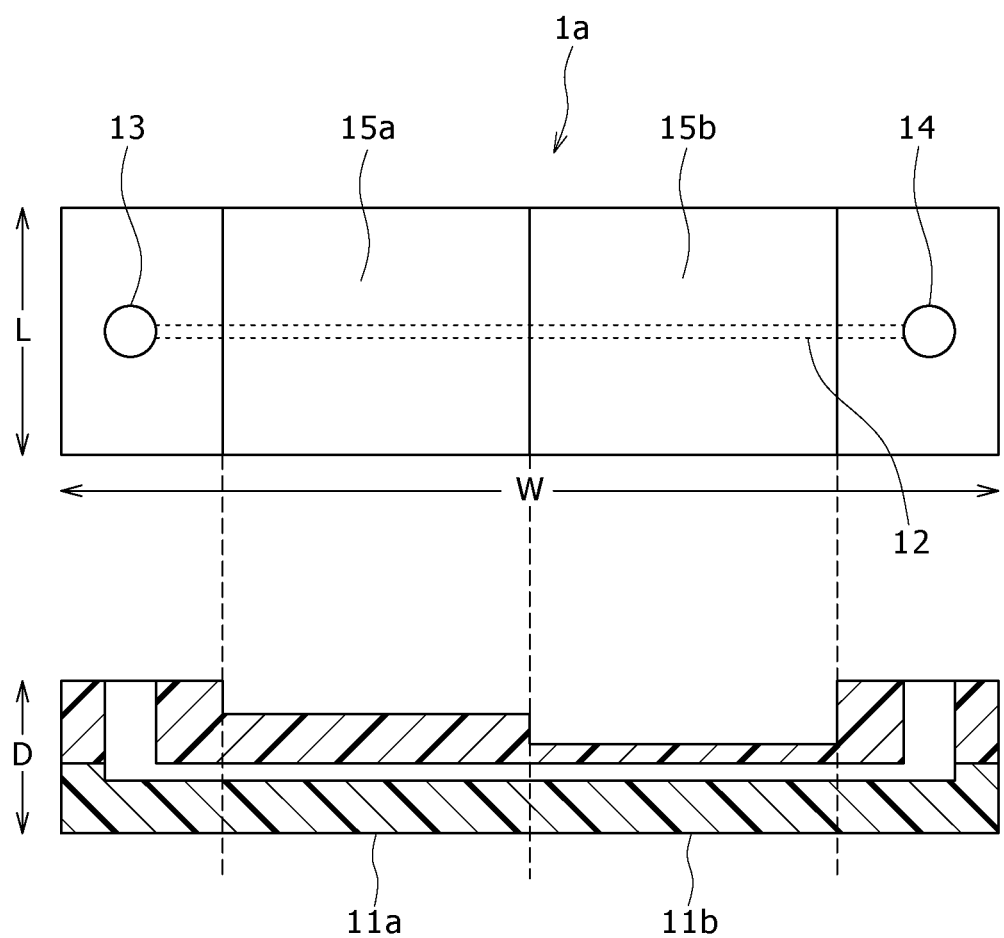
FIG. 1 is a schematic view showing a channel substrate according to a first embodiment.

The present application will be described in detail below, referring to the drawings according to an embodiment.

FIG. 1 shows a channel substrate according to a first embodiment. Referring to FIG. 1, the channel substrate 1a shown has a size set suitably in accordance with an application thereof. Typically, the channel substrate 1a may be formed with a length L of approximately 25 mm, a width W of approximately 75 mm and a thickness D of approximately 2 mm. The size mentioned is equal to the size of a popular slide glass plate and is superior in standardization. Therefore, the channel substrate 1a can be used in universal use.

The channel substrate 1a includes a plurality of detection portions 11a and 11b (which may be hereinafter referred to generally as detection portions 11), a channel 12, an introducing portion 13 for introducing a specimen into the channel 12, and a discharging portion 14 for discharging the specimen from the channel 12. The detection portions 11 include optical means to detect the specimen in the channel 12.

Detection portion surfaces 15a and 15b (which may be hereinafter referred to generally as detection portion surfaces 15) of the detection portions 11a and 11b have different distances from each other to the channel 12 on the upper face side of the channel substrate 1a. Since the distances of the detection portion surfaces 15 of the detection portions 11 to the channel 12 are different from each other, when measurement or the like of the specimen is to be carried out, a detection portion 11 having a suitable detection portion surface 15 can be selected in accordance with the type or performance of the optical measuring means.

Figure 2:
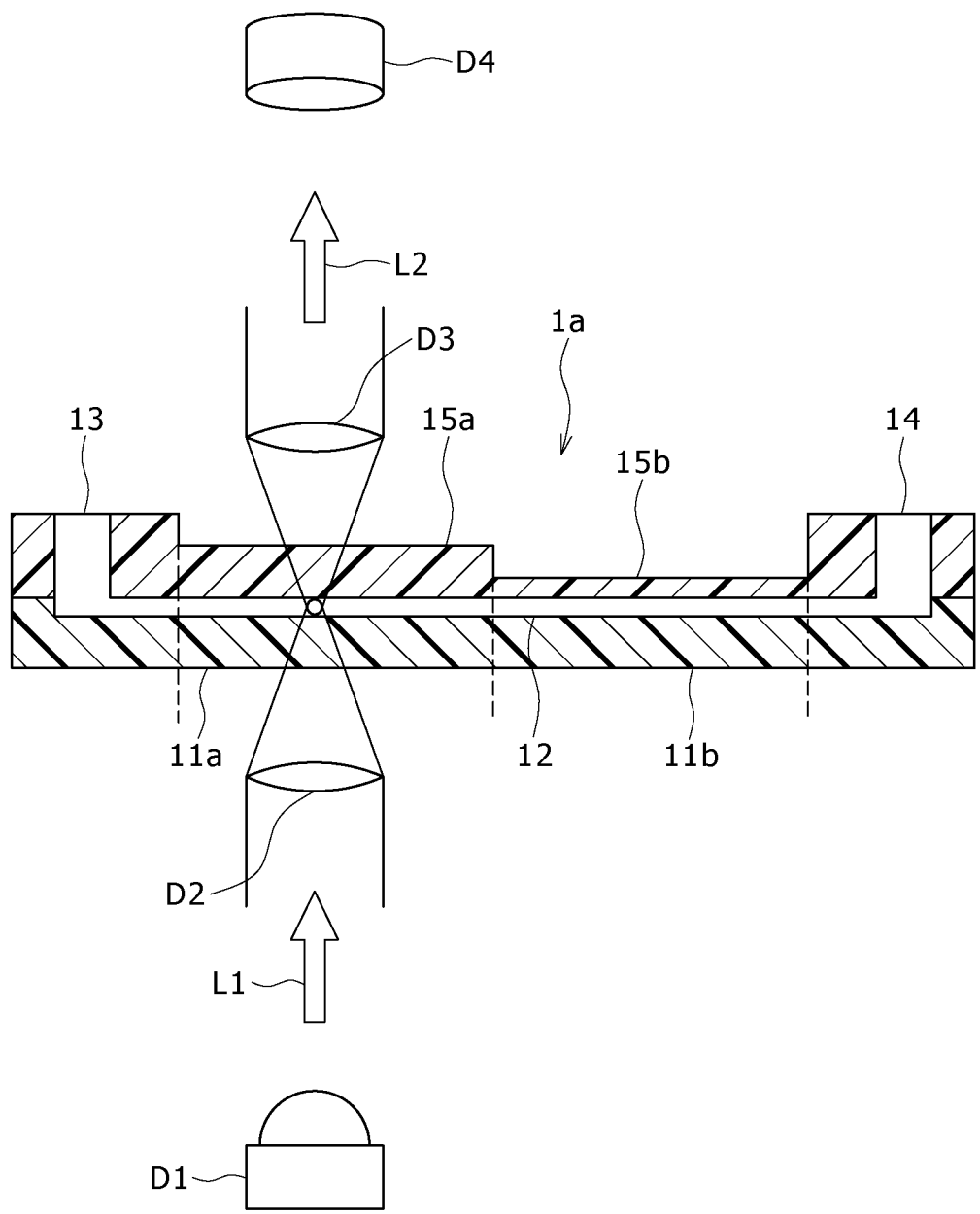
FIG. 2 is a schematic sectional view illustrating an example of detection of a specimen in a channel of the channel substrate of FIG. 1 by optical means while the specimen is circulated in the channel.
Figure 3:
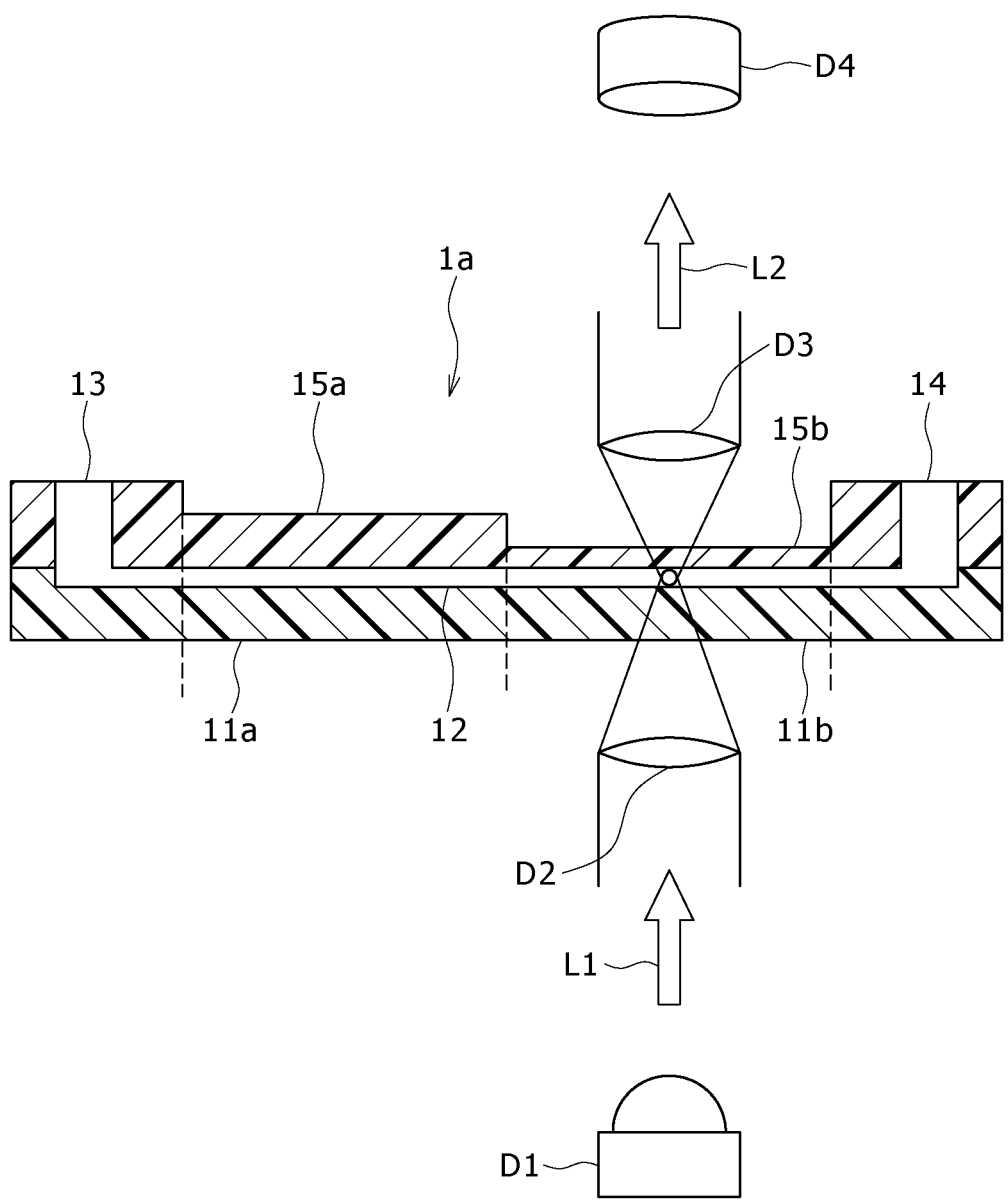
FIG. 3 is a similar view but illustrating another example of detection of a specimen in the channel of the channel substrate of FIG. 1 by the optical means while the specimen is circulated in the channel.

FIGS. 2 and 3 illustrate different manners of detection where the specimen in the channel 12 of the channel substrate 1a is detected by the optical means in a state wherein the specimen is circulated in the channel 12. In the following, an example of measurement of the specimen in the channel 12 of the channel substrate 1a by the optical means is described.

The specimen introduced from the introducing portion 13 is circulated in the channel 12 and discharged from the discharging portion 14. The detection portions 11a and 11b provided in a perpendicular direction to the circulation direction in the channel 12 have the detection portion surfaces 15a and 15b which have different distances from each other to the channel 12.

Where the numerical aperture NA of a condensing lens D3 of the detector side is small, since the working distance WD of the condensing lens D3 is comparatively long, measurement of the specimen can be detected through the detection portion 11a which has the detection portion surface 15a which has a comparatively great distance to the channel 12 as seen in FIG. 2.

An excitation ray L1 is emitted from a light source D1 provided below the lower face of the channel substrate 1a adjacent the detection portion 11a and irradiated upon the specimen circulated in the channel 12 in the channel substrate 1a through a condensing lens D2. When the excitation ray L1 is irradiated upon the specimen, fluorescent light or the like is generated from the specimen. This fluorescence L2 can be measured by a detector D4, and consequently, analysis of the specimen in the channel 12 can be carried out.

On the other hand, where the numerical aperture NA of the condensing lens D3 on the detector side is great, the working distance WD of the condensing lens D3 is comparatively short. Therefore, measurement of the specimen can be suitably carried out by the detection portion 11b which has the detection portion surface 15b which has a comparatively short distance to the channel 12 as seen in FIG. 3.

In particular, the excitation ray L1 is emitted from the light source D1 provided below the lower face of the channel substrate 1a adjacent the detection portion 11b and is irradiated upon the specimen circulated in the channel 12 in the channel substrate 1a through the condensing lens D2. As the excitation ray L1 is irradiated upon the specimen, fluorescent light or the like is generated from the specimen. This fluorescence L2 can be measured by the detector D4, and consequently, analysis of the specimen in the channel 12 can be carried out.

In an existing channel substrate, since it has a fixed thickness from the face of the substrate to the channel, a condensing lens which has a large numerical aperture NA and hence has a short working distance WD cannot be positioned sufficiently near to the channel and hence favorable measurement of the specimen cannot be carried out. However, with the channel substrate 1a of the first embodiment, since the detection portion surfaces 15a and 15b of the detection portions 11a and 11b have different distances from each other to the channel, a suitable detection portion having a suitable detection portion surface can be selectively used. Consequently, the specimen in the channel 12 can be measured with a high degree of accuracy using the suitable detection portion irrespective of the numerical aperture NA of the condensing lens of the optical measuring means.

Now, a particular configuration of the channel substrate 1a is described.

The material of the channel substrate 1a is not limited particularly, but a suitable material can be selectively used in accordance with an application of the channel substrate 1a. Particularly, a plastic material such as polycarbonate, polyolefin-based polymer or PDMS (polydimethyl siloxane), silicone rubber, a glass material such as quartz glass and so forth which are transparent with respect to visible rays and have low luminosity are suitably used.

Meanwhile, the specimen is not limited particularly in terms of the type and so forth and may be fine particles such as, for example, cells, protein or beads or fluid such as various antibodies or reagents.

The channel 12 of the channel substrate 1a is not limited particularly in terms of the length, width, depth and so forth only if it is provided in the inside of the channel substrate 1a but may have a suitable length, width, depth and so forth in accordance with an application of the channel substrate 1a.

The introducing portion 13 of the channel substrate 1a is connected to the channel 12, and the introducing portion 13 is not limited particularly in terms of the size, shape and so forth only if the introducing portion 13 can introduce the specimen into the channel 12 but may have any suitable size and shape in accordance with an application of the channel substrate 1a. Also the number of introducing portions 13 to be connected to the channel 12 is not limited particularly, but a plurality of introducing portions 13 may be connected to the single channel 12 as hereinafter described.

The discharging portion 14 of the channel substrate 1a is connected to the channel 12, and the discharging portion 14 is not limited particularly in terms of the size, shape and so forth only if the discharging portion 14 can discharge the specimen from the channel 12 but may have any suitable size and shape in accordance with an application of the channel substrate 1a. Also the number of discharging portions 14 connected to the channel 12 is not limited particularly, but a plurality of discharging portions 14 may be connected to the single channel 12 in order to separate or selectively collect specimens.

In the channel substrate 1a, the optical measuring means for measuring the specimen in the channel 12 is not limited particularly but may make use of, for example, fluorimetry, diffused light measurement, transmitted light measurement, reflected light measurement, diffracted light measurement, ultraviolet spectrometry, infrared spectrometry, Raman spectrometry, FRET measurement, FISH measurement and other various fluorescence spectral measurements. For example, where fluorimetry is to be carried out, a fluorescent dye can be used, and if fluorescent dyes having different excitation wavelengths are used, then the accuracy in detection can be enhanced.

Further, the optical measuring means is not limited particularly in terms of the configuration to that shown in FIGS. 2 and 3, but may be configured such that the light source D1 is provided above the upper face of the channel substrate 1a while the detector D4 is provided below the lower face of the channel substrate 1a which is not shown in FIGS. Or, the optical measuring means may be configured such that both of the light source D1 and the detector D4 are disposed on the same side with respect to the plane of the channel substrate 1a.

Furthermore, the optical measuring means is not limited particularly in terms of the numerical aperture NA of the condensing lens, and the channel substrate 1a can be ready for a condensing lens having a numerical aperture NA over a wide range. For example, where the distance from the detection portion surface 15 to the channel 12 is approximately 0.1 mm, a condensing lens whose numerical aperture NA ranges approximately from 0.7 to 0.9 can be used. Meanwhile, where the distance from the detection portion surface 15 to the channel 12 is approximately 0.6 mm, a condensing lens whose numerical aperture NA ranges approximately from 0.5 to 0.7 can be used. Further, where the distance from the detection portion surface 15 to the channel 12 is approximately 1 mm, a condensing lens whose numerical aperture NA ranges from approximately 0.1 to 0.5 can be used.

Further, for example, where the distance from the detection portion surface 15 to the channel 12 is as short as less than approximately 0.1 mm, an immersion optical system which is used for detection while water, oil, gel or the like having a high refractive index is placed on the substrate, a microlens optical system which is used for detection while an optical lens is placed on the substrate and some other optical system can be suitably combined to carry out detection by the optical means.

In the channel substrate 1a, the specimen in the channel 12 can be used for various processes other than optical measurement. The "processes" are not limited particularly in terms of the contents and may be various measuring processes, detection processes, separation processes, reaction processes and so forth. For example, measurement, detection and so forth of an electric property, a magnetic property and so forth can be carried out in addition to optical measurement. Also it is possible to dispense or recover the specimen extracted from the discharging portion 14 based on information obtained by the optical measurement.

Figure 4:
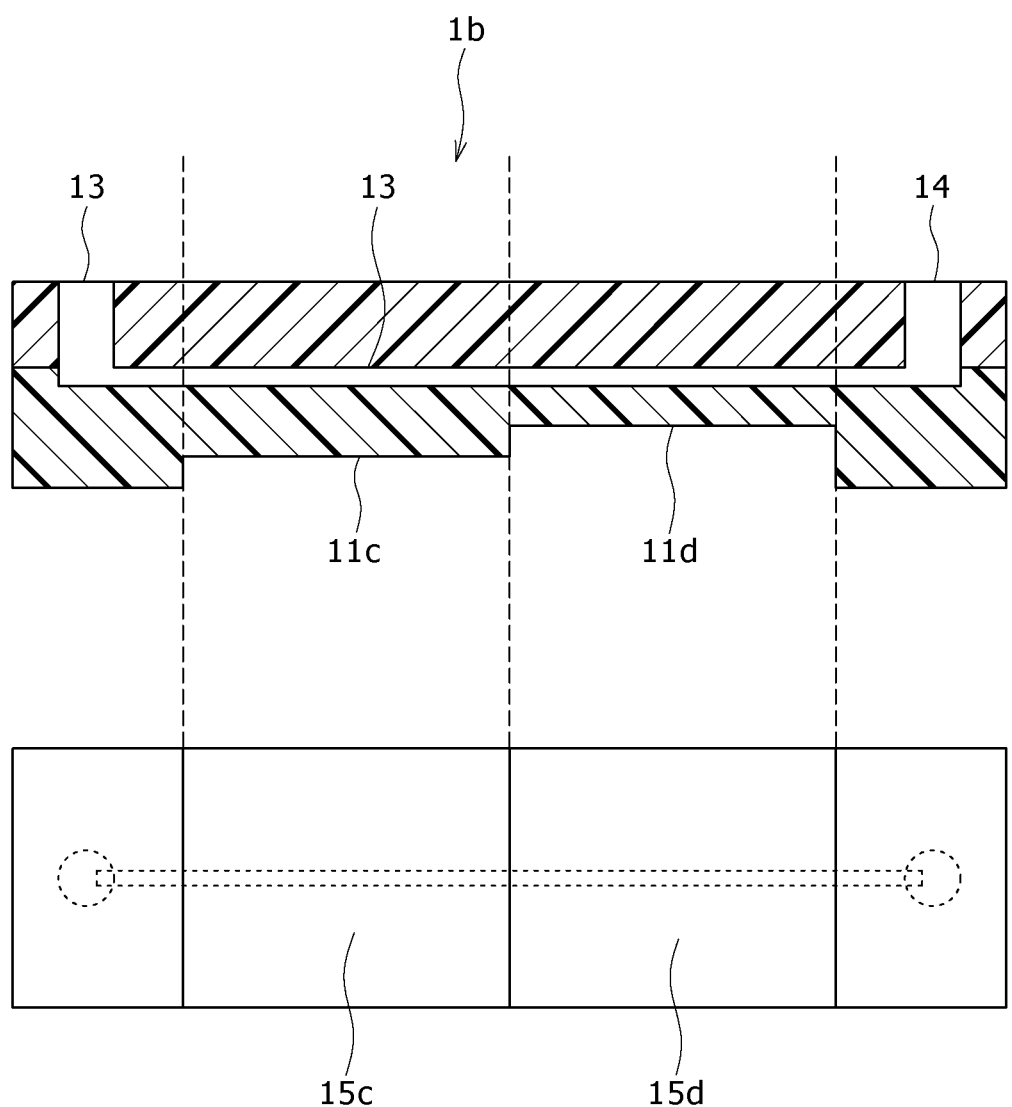
FIGS. 4 and 5 are schematic views of different forms of the channel substrate of FIG. 1 according to the first embodiment which are different from the channel substrate of FIG. 1.

In the channel substrate 1a, the detection portions 11 are not limited particularly in terms of the detection portion surfaces 15 only if the distances from the detection portion surfaces 15 to at least one of the opposite faces of the channel substrate 1a are different from each other. For example, referring to FIG. 4, the detection portions 11c and 11d may have detection portion surfaces 15c and 15d having distances different from each other to the channel 12 on the lower face side of the channel substrate 1a. In this instance, one of the detection portions 11 which has a suitable detection portion surface 15 can be selected in response to the numerical aperture NA of the condensing lens D3 of the detector side.

Figure 5:
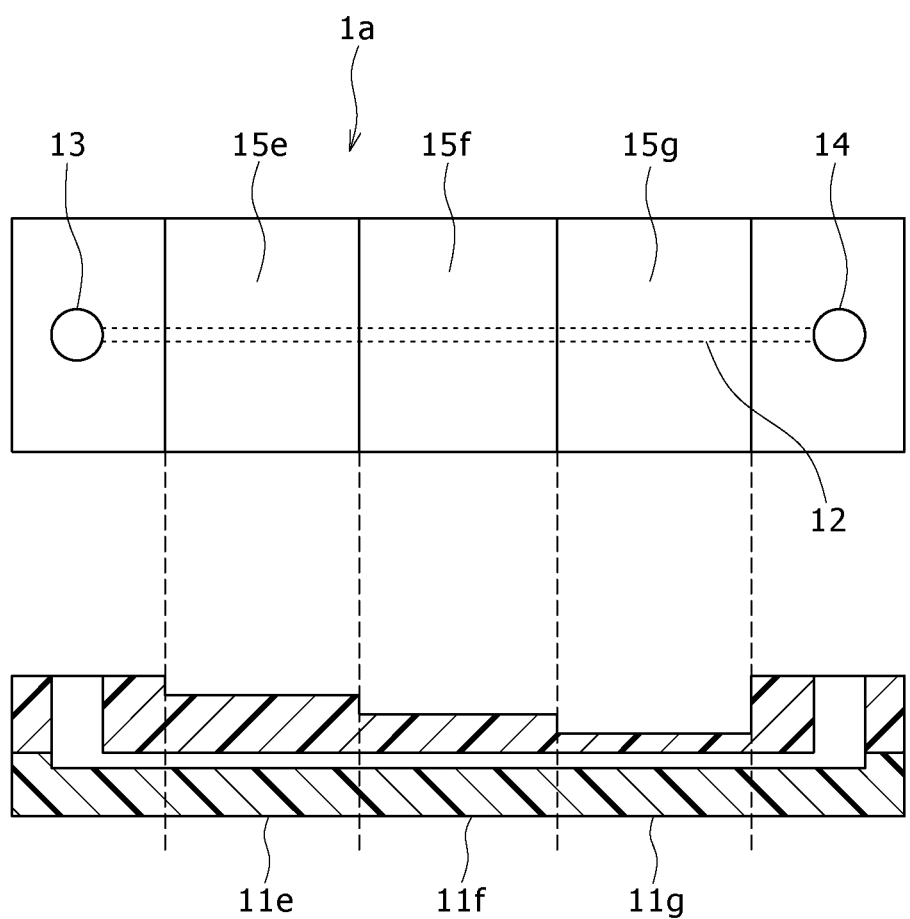

Further, in the channel substrate 1a, the number of detection portions 11 can be set suitably in accordance with an application of the channel substrate 1a and so forth. For example, three detection portions 11e, 11f and 11g having detection portion surfaces 15e, 15f and 15g whose distances to the channel 12 are different from each other may be provided on the upper face side of the channel substrate 1a as seen in FIG. 5. The channel substrate 1a is not limited particularly also in terms of the area of the detection portion surfaces 15 or the distance of the detection portion surfaces 15 from the channel 12, and they can be designed suitably in response to a performance of the optical detection system, an application of the channel substrate 1a and so forth. For example, though not shown, one of the detection portion surfaces 15 having different distances from each other to the channel 12 may be provided in the same plane as the face of the channel substrate 1a.

Figure 6:
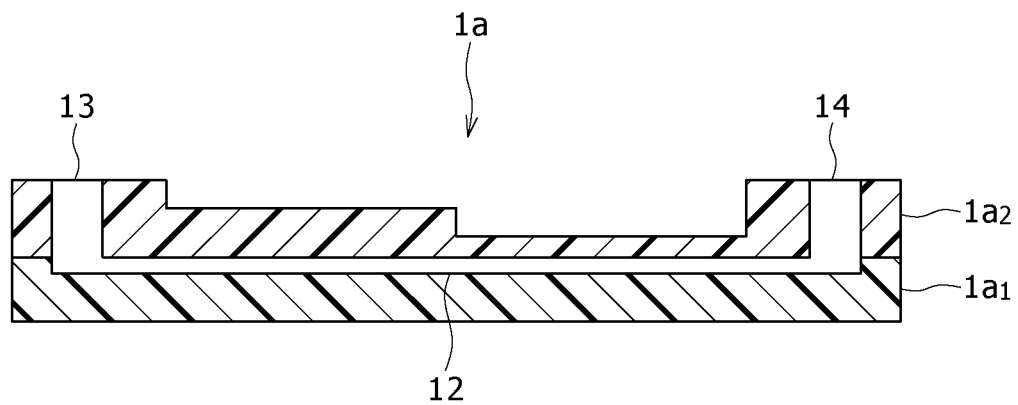
FIG. 6 is a schematic view illustrating an example of a fabrication method of the channel substrate of FIG. 1.
Figure 6:
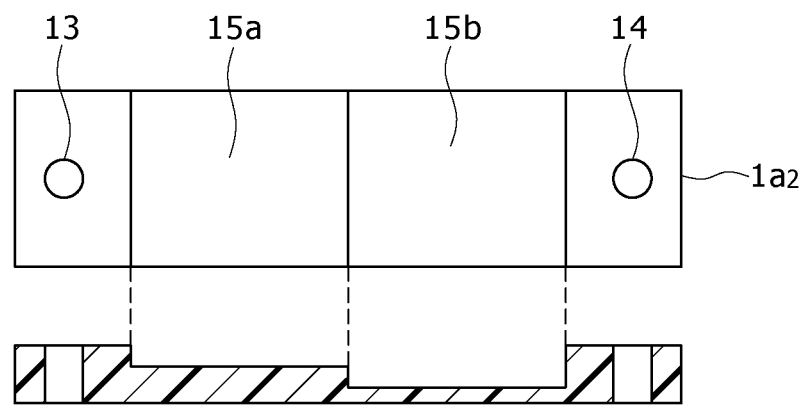
Figure 6:
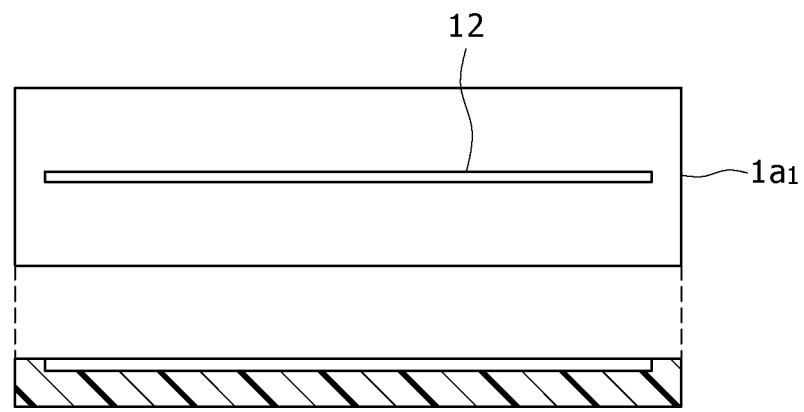

An example of a fabrication method of the channel substrate 1a is described. FIG. 6 illustrates an example of the fabrication method of the channel substrate 1a. The channel substrate 1a can be fabricated simply and readily by injection molding using a double-sided metal mold, mechanical working using a micro-drill or the like. The channel substrate 1a having the channel 12 can be obtained from two substrates $1a_1$ and $1a_2$.

The substrate $1a_1$ forms the first layer and has a groove formed on the upper surface thereof and corresponding to the channel 12.

The substrate $1a_2$ forms the second layer and has two or more detection portion surfaces 15a and 15b formed on the upper face thereof and having distances different from each other to the lower face of the channel substrate 1a. The introducing portion 13 and the discharging portion 14 are formed in the substrate $1a_2$ in such a manner as to extend to the lower face of the substrate $1a_2$.

By laminating the substrate $1a_2$ on the upper face of the channel substrate 1a of the lower layer, the channel substrate 1a having the channel 12 can be formed.

The substrates $1a_1$ and $1a_2$ can be fabricated by a known technique. For example, through not shown, the substrate $1a_1$ can be fabricated using a technique that an upper metal mold and a lower metal mold which have a channel shape portion are set in position on an injection molding machine to carry out shape transfer to the channel substrate 1a. The channel substrate 1a obtained by the injection molding has a channel shape portion formed thereon.

Further, the substrates $1a_1$ and $1a_2$ can be laminated to each other suitably using a related art technique. For example, heat sealing, an adhesive, anodic bonding, bonding using an adhesive sheet, plasma activation bonding, ultrasonic bonding and so forth can be used suitably for the lamination. A suitable lamination technique can be selected taking the material, shape and physical property of the substrate into consideration.

Further, though not shown, a step of carrying out surface working for the surface of the substrates $1a_1$ and $1a_2$ after the injection molding can be adopted. By the step, also such a physical property as a hydrophobic property of the surface of the channel 12 can be controlled.

It is to be noted that the fabrication method of the substrate is not limited to the double-sided molding, but such a technique as single-sided molding can be adopted. Although, as the technique for single-sided molding, such an existing method as plate punching can be used suitably, preferably double-sided molding is used from the point of view of the accuracy in molding and so forth. In this manner, where the channel structure according to a first embodiment is adopted, a channel substrate which can achieve fluid control of a high degree of accuracy can be fabricated by a simple and convenient method such as injection molding by a double-sided metal mold. In this manner, the channel structure and the channel substrate according to the first embodiment are advantageous also in fabrication thereof.

Upon fabrication of the channel substrate, a suitable material or a suitable technique can be used for injection molding. The substrate can be fabricated using a resin material or the like which can be used for molding, and the type of the material is not limited particularly and, for example, a thermoplastic resin material can be used. In particular, polymethyl methacrylate or a silicone resin material can be used. Where spectroscopic analysis is carried out on the channel substrate, preferably a light transmitting resin is used. Further, an injection molded substrate using low melting point glass, a nano imprinting technique using an ultraviolet curing resin and so forth can be used.

Figure 7:
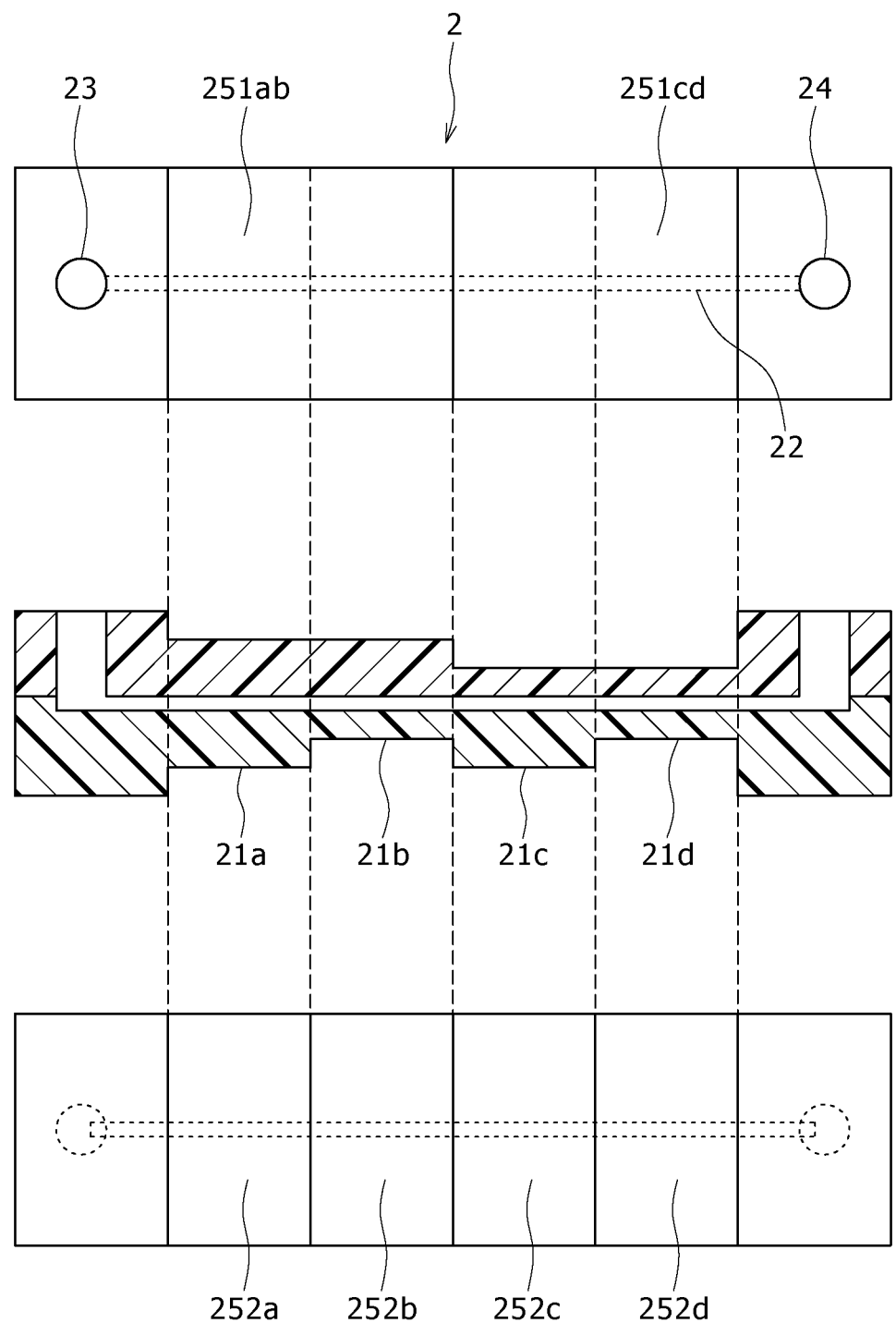
FIGS. 7, 8 and 9 are schematic views of channel substrates according to second, third and fourth embodiments, respectively.

FIG. 7 shows a channel substrate according to a second embodiment. In the following, only differences of the second embodiment from the first embodiment are described while description of common portions of them is omitted herein to avoid redundancy.

Referring to FIG. 7, the channel substrate 2 according to the second embodiment includes a plurality of detection portions 21a, 21b, 21c and 21d (which may be hereinafter referred to generally as detection portions 21), a channel 22, an introducing portion 23 for introducing a specimen into the channel 22, and a discharging portion 24 for discharging the specimen from the channel 22. The detection portion 21 uses optical means to detect the specimen in the channel 22.

Detection portion surfaces 251*ab* and 251*cd* (which may be hereinafter referred to generally as detection portion surfaces 251) of the detection portions 21*a*, 21*b*, 21*c* and 21*d* are provided on the upper face of the channel substrate 2 and have distances different from each other to the channel 22. Meanwhile, detection portion surfaces 252*a*, 252*b*, 252*c* and 252*d* (which may be hereinafter referred to generally as detection portion surfaces 252) of the detection portions 21*a*, 21*b*, 21*c* and 21*d* are provided on the lower face of the channel substrate 2 and have distances different from each other to the channel 22. It is to be noted that the detection portion surfaces 251*ab*, 251*cd*, 252*a*, 252*b*, 252*c* and 252*d* may be hereinafter referred to generally as detection portion surfaces 25.

Since the distances of the detection portion surfaces 25 of the detection portions 21 to the channel 22 are different on the opposite faces of the channel substrate 2, a detection portion 21 having a detection portion surface 25 which is suitable for both of the numerical aperture NA of the condensing lens D3 on the detector side and the numerical aperture NA of the condensing lens D2 on the light source side can be used to carry out detection by the optical means.

As an example, a particular example wherein the light source D1 is provided on the lower face side of the channel substrate 2 and the detector D4 is provided on the upper face side of the channel substrate 2 while excitation ray L1 is irradiated upon the specimen in the channel 22 from below the lower face of the channel substrate 2 and fluorescence L2 generated from the specimen in the channel 22 is detected from above the upper face of the substrate is described.

The detection portion surfaces on the upper face side of the channel substrate 2 are determined in response to the numerical aperture NA of the condensing lens D3 on the detector side. Where the numerical aperture NA of the condensing lens D3 on the detector side is comparatively small, since the working distance WD of the condensing lens D3 is comparatively long, detection can be carried out by the optical means using the detection portions 21*a* and 21*b* having the detection portion surface 251*ab* which has a comparatively great distance to the channel 22. Meanwhile, where the numerical aperture NA of the condensing lens D3 on the detector side is comparatively great, since the working distance WD of the condensing lens D3 is comparatively short, detection can be carried out by the optical means using the detection portions 21*c* and 21*d* having the detection portion surface 251*cd* which has a small distance to the channel 22.

Then, the detection portion surfaces on the lower face side of the channel substrate 2 are determined in response to the numerical aperture NA of the condensing lens D2 on the detector side. Where the numerical aperture NA of the condensing lens D2 on the detector side is comparatively small, since the working distance WD of the condensing lens D2 is comparatively long, the excitation ray can be irradiated at the detection portions 21*a* and 21*b* having the detection portion surfaces 252*a* and 252*c* which have a comparatively great distance to the channel 22. Meanwhile, where the numerical aperture NA of the condensing lens D2 on the detector side is comparatively great, since the working distance WD of the condensing lens D2 is comparatively short, the excitation ray can be irradiated at the detection portions 21*c* and 21*d* having the detection portion surfaces 252*b* and 252*d* which have a comparatively small distance to the channel 22.

In this manner, the position on the channel substrate 2 at which optical measurement can be carried out suitably is determined depending upon a combination of a numerical aperture NA of the condensing lens D3 on the detector side and a numerical aperture NA of the condensing lens D2 on the light source side. A relationship between the performances of the condensing lens D3 on the detector side and the condensing lens D2 on the light source side and a suitable detection portion 21 is illustrated in Table 1.

TABLE 1

| | | | | |
|---|---|---|---|---|
| Numerical aperture NA of detector side condensing lens | small | small | large | large |
| Distance from detection portion surface on upper face of substrate to channel | large | large | small | small |
| Distance from detection portion surface on lower face of substrate to channel | large | small | large | small |
| Numerical aperture NA of light source side condensing lens | small | large | small | large |
| Suitable detection portion selected in FIG. 7 | 21a | 21b | 21c | 21d |

In the channel substrate 2 according to the present embodiment, the detection portion surfaces 251*ab* and 251*cd* of the detection portions 21*a*, 21*b*, 21*c* and 21*d* are provided on the upper face of the channel substrate 2 and have distances different from each other to the channel 22. Meanwhile, the detection portion surfaces 252*a*, 252*b*, 252*c* and 252*d* are provided on the lower face of the channel substrate 2 and have distances different from each other to the channel 22. Therefore, by selecting a detection portion 21 having a detection portion surface 25 suitable for both of the performance of the condensing lens D2 on the light source side and the performance of the condensing lens D3 on the detector side, detection by the optical means can be carried out with a higher degree of accuracy.

It is to be noted that, where the detection portion surfaces 25 of the detection portions 21 have different distances from each other to the channel 22 on the lower face side of the channel substrate 2, the number, area and so forth of the detection portions 21 of the channel substrate according to the present embodiment are not limited to those of the channel substrate 2 shown in FIG. 7. For example, the number of detection portions 21 can be set suitably in accordance with an application of the channel substrate 2 and so forth. Further, also the area of the detection portion surfaces 25 or the distance of the detection portion surfaces 25 to the channel 22 may be different between the detection portion surfaces 251 on the upper face side of the channel substrate 2 and the detection portion surfaces 252 on the lower face side of the channel substrate 2.

Figure 8:
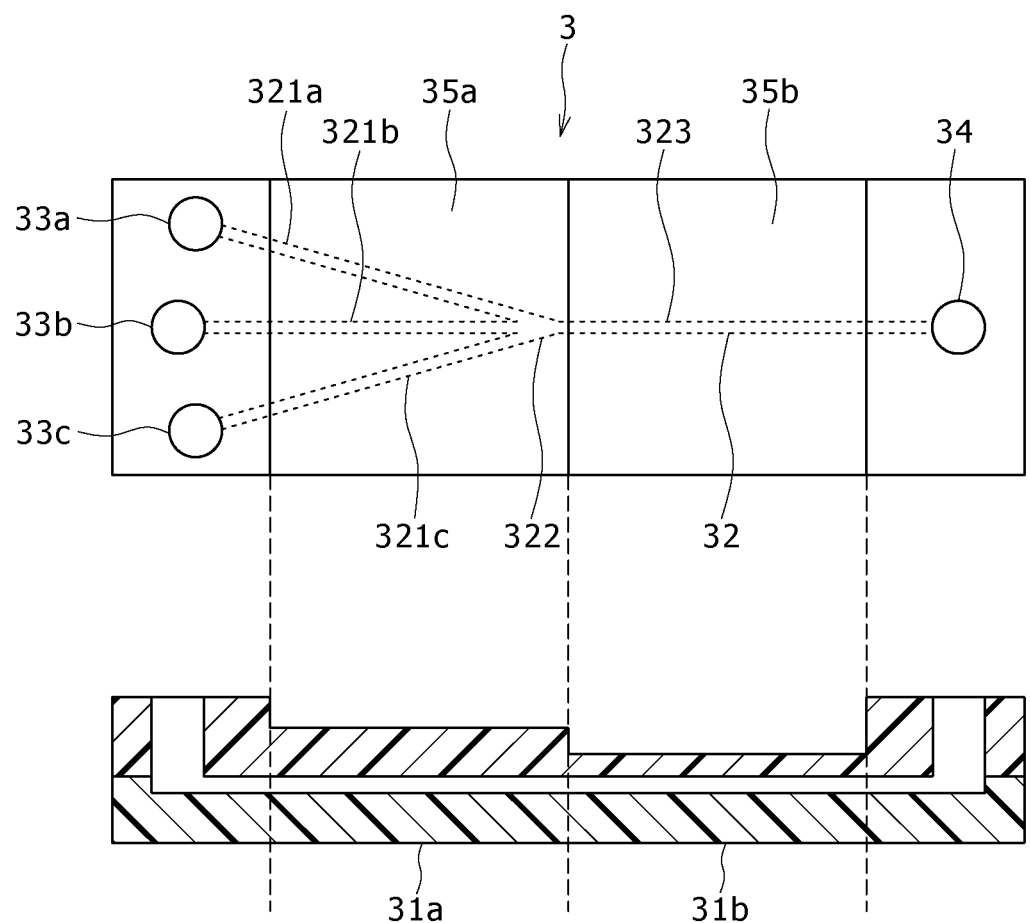

FIG. 8 shows a channel substrate according to a third embodiment. In the following, only differences of the third embodiment from the first or second embodiment are described while description of common portions of them is omitted herein to avoid redundancy.

Referring to FIG. 8, the channel substrate 3 according to the third embodiment includes a plurality of detection portions 31*a* and 31*b* (which may be hereinafter referred to generally as detection portions 31), a channel 32, three introducing portions 33*a*, 33*b* and 33*c* for introducing a specimen into the channel 32, and a discharging portion 34 for discharging the specimen from the channel 32. Each detection portion 31 uses optical means to detect the specimen in the channel 32.

The introducing portions 33*a*, 33*b* and 33*c* are connected to branch paths 321*a*, 321*b* and 321*c* provided in the channel 32 and are communicated at a joining portion 322 with a main flow path 323.

The detection portion 31*a* is provided perpendicularly to the flowing direction in the branch paths 321*a*, 321*b* and 321*c*, and the detection portion 31*b* is provided perpendicularly to the flowing direction in the main flow path 323. The detection portion surfaces 35a and 35b of the detection portions 31a and 31b are provided on the upper face of the channel 32 and have distances different from each other to the channel 32.

Since two or more introducing portions 33a, 33b and 33c are connected to the channel 32, a plurality of specimens can be introduced into the channel 32. Consequently, the channel substrate 3 can be used for a wide variety of applications such as a micro reactor, a micro analyzer, a flow cytometry and so forth.

Further, the channel substrate 3 is configured such that the detection portion 31a is provided perpendicularly to the flowing direction in the branch paths 321a, 321b and 321c and the detection portion 31b is provided perpendicularly to the flowing direction in the main flow path 323 while the detection portion surfaces 35a and 35b of the detection portions 31a and 31b have distances different from each other to the channel 32 on the upper face side of the channel substrate 3. Therefore, also where the optical measuring means exhibits different performances before and after specimens introduced from the introducing portions 33a, 33b and 33c are joined with each other at the joining portion 322, detection can be carried out suitably by the optical means.

Generally, where an interaction of a plurality of specimens is observed in a channel substrate, analysis of the specimens after they are joined with each other requires a high degree of accuracy in comparison with analysis of the individual specimens before they are joined with each other. Thereupon, since the channel substrate 3 includes the detection portion 31b having the detection portion surface 35a which has a comparatively small distance to the channel 32 in the direction perpendicular to the flowing direction in the main flow path 323 after the joining, even where the numerical aperture NA of the condensing lens is small, detection can be carried out suitably by the optical means.

The specimens to be introduced from the introducing portions 33a, 33b and 33c are not limited particularly and may be fine particles such as, for example, cells, protein or beads or fluid such as various antibodies or reagents.

Or, sheath liquid may be introduced from the introducing portions 33a and 33c such that a specimen introduced from the introducing portion 33b is sandwiched and transported by the sheath liquid. The type and so forth of the sheath liquid are not limited particularly, and suitable liquid can be selected taking a nature and so forth of a specimen to be used into consideration. Further, additive or the like may be added as occasion demands.

For example, in the field of the flow cytometry, cells, protein, beads and so forth can be used as a specimen while sheath liquid such as physiological salt solution can be used as fluid. On the other hand, where the channel substrate 3 is used for various analyzers or micro reactors, if various kinds of oil, organic solvent and electrolyte or the like are used as the sheath liquid, then crystallization of nano emulsion, nano capsules or various samples, chemical synthesis of dangerous substances, component analysis and so forth can be carried out.

Figure 9:
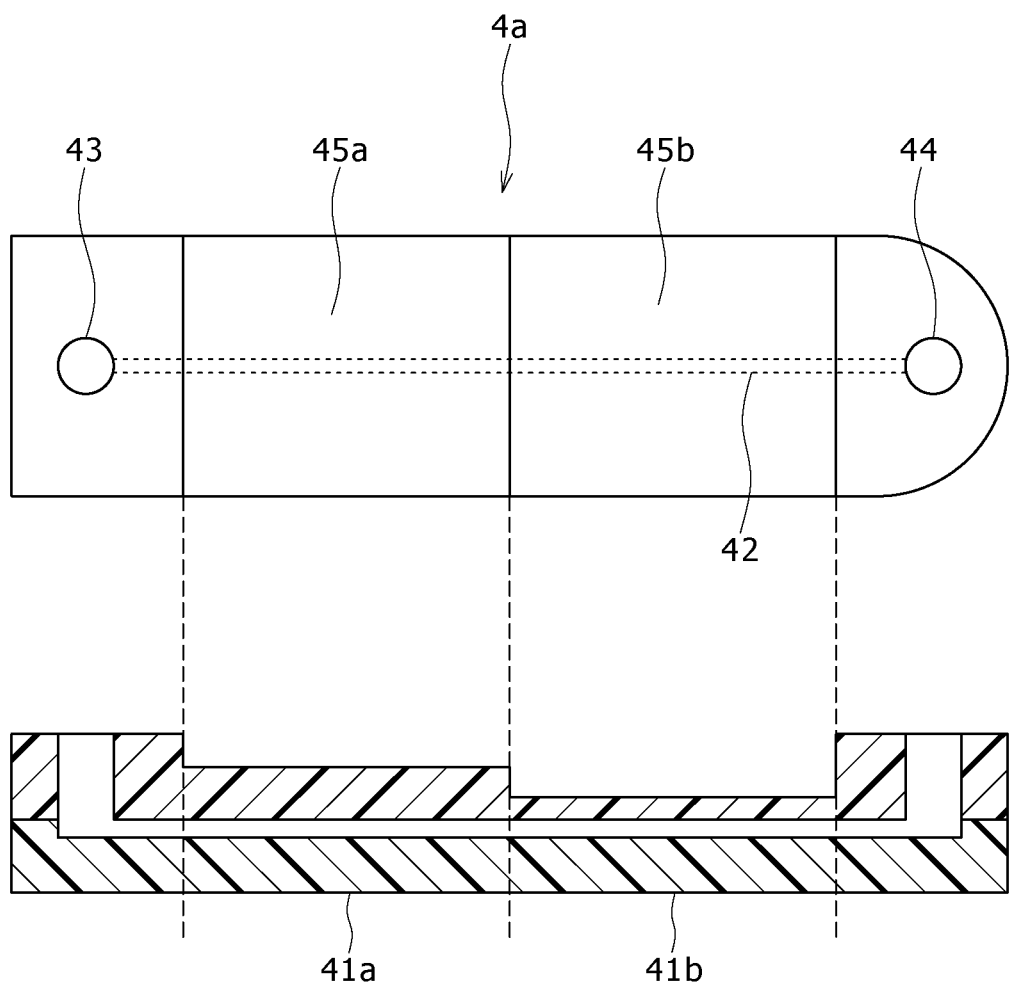

FIG. 9 shows a channel substrate according to a fourth embodiment. In the following, only differences of the third embodiment from the first to third embodiments are described while description of common portions of them is omitted herein to avoid redundancy.

Referring to FIG. 9, the channel substrate 4a according to the present embodiment includes a plurality of detection portions 41a and 41b (which may be hereinafter referred to generally as detection portions 41), a channel 42, an introducing portion 43 for introducing a specimen into the channel 42, and a discharging portion 44 for discharging the specimen from the channel 42. Each detection portion 41 uses optical means to detect a specimen in the channel 42.

Detection portion surfaces 45a and 45b (which may be hereinafter referred to generally as detection portion surfaces 45) of the detection portions 41a and 41b have distances different from each other to the channel 42 on the upper face side of the channel substrate 4a. Since the detection portion surfaces 45a and 45b of the detection portions 41a and 41b have distances different from each other to the channel 42 on the upper face side of the channel substrate 4a, upon measurement of the specimen or the like, a suitable detection portion surface can be selected in response to the type or performance of the optical measuring means.

A semicircular shape is formed at one end portion of the upper face side of the channel substrate 4a. The shape mentioned is provided as an identification shape from which information regarding the substrate can be identified.

Where the identification shape from which information regarding the substrate can be identified is provided on the channel substrate, information of the direction or the like of the channel provided on the substrate can be identified. For example, such a situation that the introduction direction of a specimen is mistaken or the installation direction of the substrate upon optical measurement is mistaken can be prevented. Further, by changing the identification shape depending upon the type of the substrate, it is possible to prevent wrong use of the substrate or the like.

Figure 10:
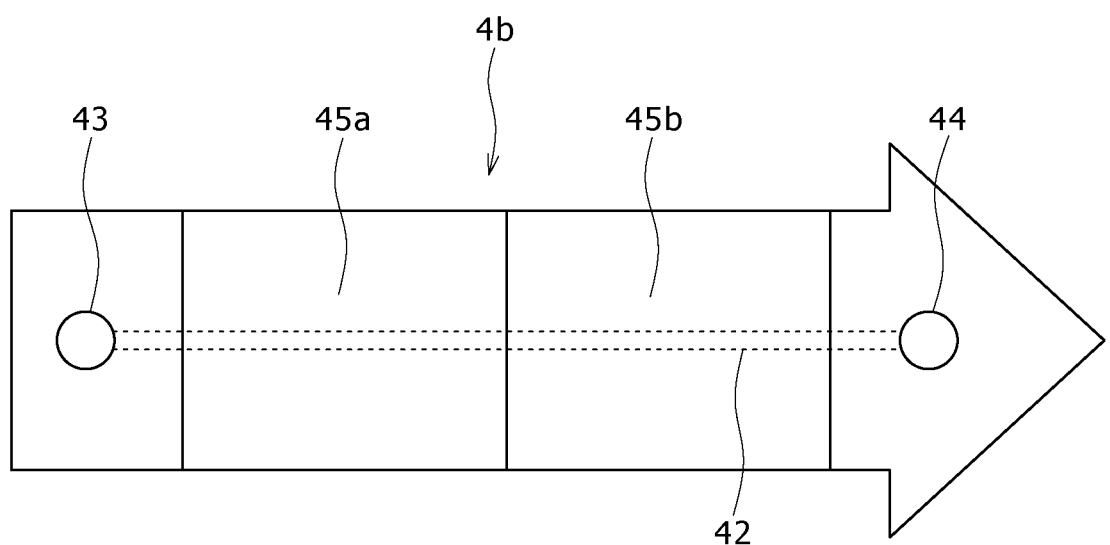
FIGS. 10 and 11 are schematic views of different examples of the channel substrate according to the fourth embodiment which are different from the channel substrate of FIG. 9.
Figure 11:
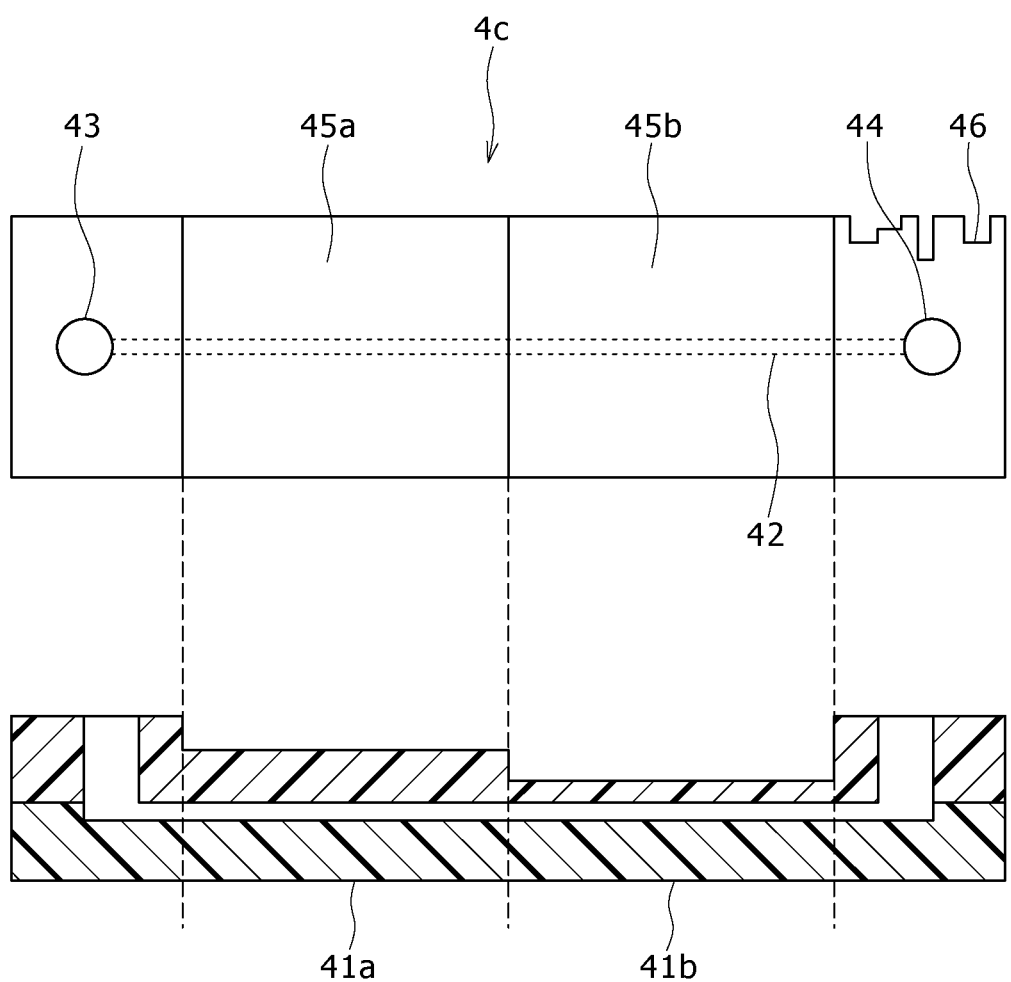

The identification shape is not limited to the semicircular shape shown in FIG. 9, but may be, for example, such an arrow shape as seen in FIG. 10 or the like. Further, a cutaway shape 46 may be provided on a side face of the substrate like such a channel substrate 4c as shown in FIG. 11. Also the size and so forth of the identification are not limited particularly.

The method of formation of the identification shape is not limited particularly, and the identification shape may be formed simultaneously with fabrication of the substrate by injection molding by forming a shape for the identification shape formed in advance on a metal mold. Further, in order to obtain a desired shape, the shape may be formed by mechanical working by a micro drill or the like after the fabrication of the substrate.

The portion at which the identification shape is to be provided is not limited particularly if information regarding the substrate can be identified based on the difference of the shape. The identification shape may be provided on a side face of the substrate like the channel substrate 4a or on the upper face or the lower face of the substrate. For example, where the information regarding the substrate is identified through visual observation, preferably the identification shape is provided at a position of the substrate at which the identification shape can be identified when the substrate is viewed from above. Further, the number of such identification shapes to be provided on one channel substrate is not limited particularly, but a plurality of identification shapes may be provided.

Further, the information to be identified from the identification shape is not limited particularly, and, for example, information regarding the direction of the substrate, information regarding the type of the substrate, information regarding the size of the substrate or information regarding the detection portion surfaces provided on the substrate may be applied as the information to be identified. The number of kinds of the information to be identified may be one, two or more.

The method of identifying the identification shape is not limited particularly, and the identification shape may be identified through visual observation or by means of a scanner, a sensor or the like. For example, the cutaway shape 46 of the channel substrate 4c shown in FIG. 11 can be formed so as to allow composite identification of such various kinds of information regarding the substrate mentioned above by suitably designing the shape, position and so forth of the cutaway shape 46. The cutaway shape 46 can be read by a scanner, a sensor or the like to obtain the information regarding the substrate.

For example, referring to FIG. 11, information regarding the position of detection portion surfaces 44a and 44b and/or the distance from the detection portion surfaces 45a and 45b to the channel 42 is coded on the cutaway shape 46 provided on the channel substrate 4c. If the cutaway shape 46 is read by a scanner, a sensor or the like provided in an optical detector, then the position or the like of the substrate at which optical measurement should be carried out can be determined based on the thus read information.

Or, for example, the optical measuring means may include a shape complementary to the cutaway shape 46 provided on a particular channel substrate such that optical measurement can be carried out only when the shape on the optical measuring means side and the cutaway shape 46 of the substrate side are found complementary to each other.

In other words, the cutaway shape 46 provided on the channel substrate may function as a bar code representative of information regarding the substrate or may cooperate with the shape provided on an external apparatus or the like such that they function like a key and a keyhole.

Figure 12:
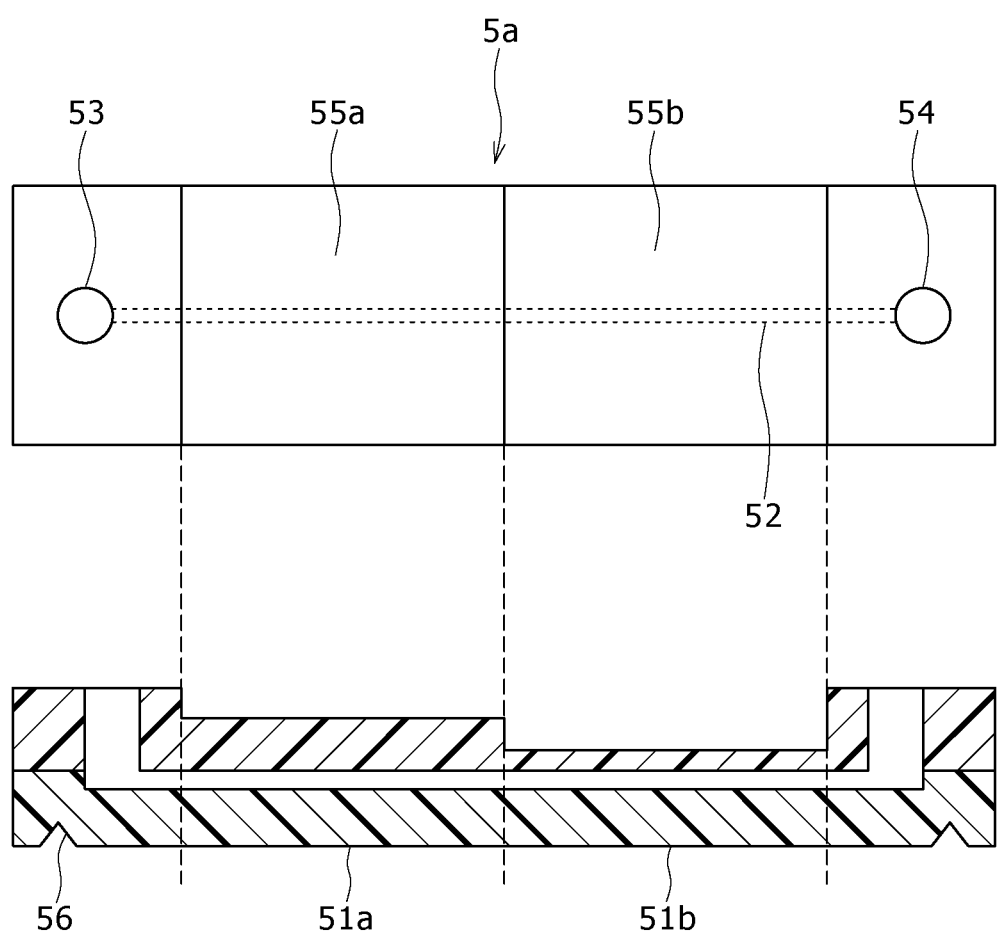
FIG. 12 is a schematic view of a channel substrate according to a fifth embodiment.

FIG. 12 shows a channel substrate according to a fifth embodiment. In the following, only differences of the fifth embodiment from the first to fourth embodiments are described while description of common portions of them is omitted herein to avoid redundancy.

Referring to FIG. 12, the channel substrate 5a according to the fifth embodiment includes a plurality of detection portions 51a and 51b (which may be hereinafter referred to generally as detection portions 51), a channel 52, an introducing portion 53 for introducing a specimen into the channel 52, and a discharging portion 54 for discharging the specimen from the channel 52. Each detection portion 51 includes optical means to detect the specimen in the channel 52.

Detection portion surfaces 55a and 55b (which may be hereinafter referred to generally as detection portion surfaces 55) of the detection portions 51a and 51b have distances different from each other to the channel 52 on the upper face side of the channel substrate 5a. Since the detection portion surfaces 55a and 55b of the detection portions 51a and 51b have distances different from each other to the channel 52 on the upper face side of the substrate, upon measurement or the like of a specimen, a suitable detection portion surface can be selected in response to the type or the performance of the optical measuring means.

On the lower face side of the channel substrate 5a, two positioning shapes 56 in the form of recess grooves are formed. The positioning shapes 56 are provided for defining the position of the channel substrate 5a when the channel substrate 5a is to be installed.

Where the positioning shape 56 with which the position of the channel substrate 5a can be fixed upon installation of the channel substrate 5a is provided on the channel substrate 5a, upon transportation of the channel substrate 5a or upon processing of a specimen in the detection portion 51, it is possible to define the direction of the channel substrate 5a or prevent the channel substrate 5a from being brought out of position.

The shape of the positioning shape 56 is not limited to that shown in FIG. 12 but can be designed suitably in response to the shape or the like of the place at which the channel substrate 5a is to be installed. For example, if the positioning shape 56 is shaped so as to be complementary with a substrate fixing jig provided on the optical measuring means or the like, then it is possible to define the direction of the substrate or prevent displacement of the channel substrate 5a when optical measurement of the channel substrate 5a is to be carried out. Also the size and so forth of the positioning shape 56 is not limited particularly.

The method of formation of the positioning shape 56 is not limited particularly, and the positioning shape 56 may be formed simultaneously with fabrication of the channel substrate 5a by injection molding by forming a shape complementary to the positioning shape 56 on a metal mold in advance. Further, in order to obtain a desired shape, the positioning shape 56 may be formed by mechanical working using a micro drill or the like after the fabrication of the substrate.

The portion at which the positioning shape 56 is provided is not limited particularly if it allows the channel substrate 5a to be fixed in position upon installation of the channel substrate 5a. The positioning shape 56 may be provided on the lower face of the substrate like the channel substrate 5a or may otherwise be provided on the lower face or a side face of the substrate. Further, the number of such positioning shapes 56 to be provided on one channel substrate is not limited particularly, and a plurality of positioning shapes 56 may be provided.

Figure 13:
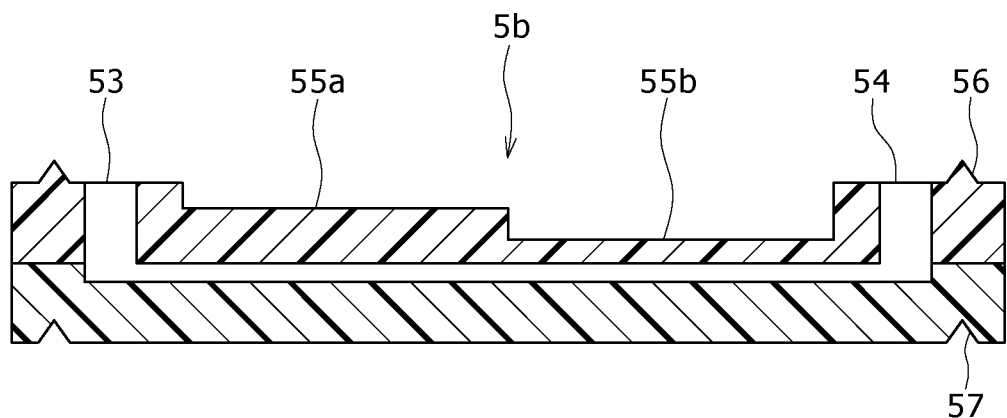
FIG. 13 is a schematic view of a different example of the channel substrate according to the fifth embodiment which is different from the channel substrate of FIG. 12.
Figure 14:
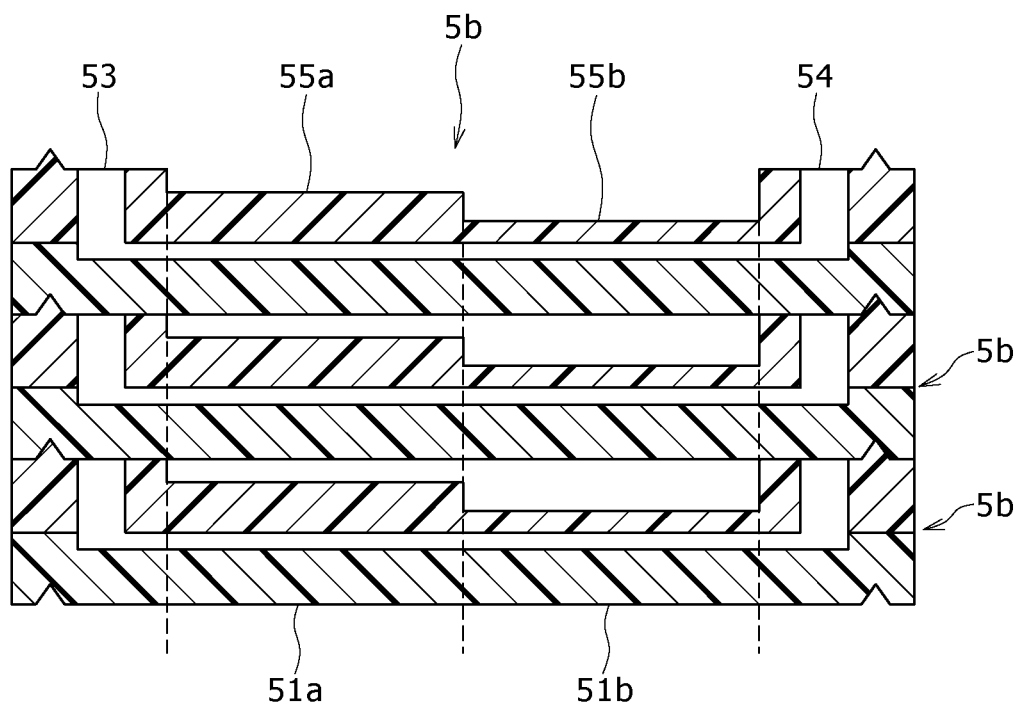
FIG. 14 is a schematic view showing a laminate of a plurality of channel substrates shown in FIG. 13.
Figure 15:
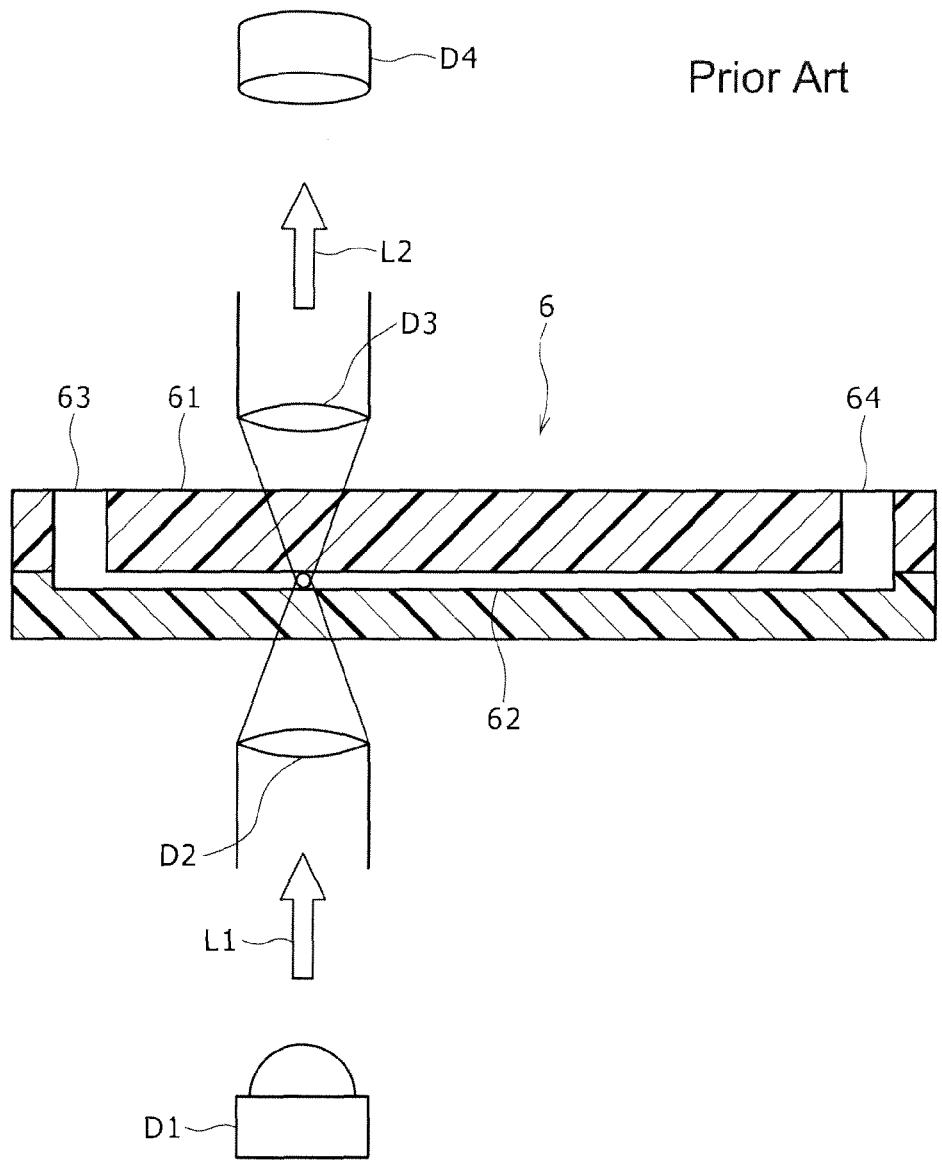
FIG. 15 is a schematic view showing an existing channel substrate.
Figure 16:
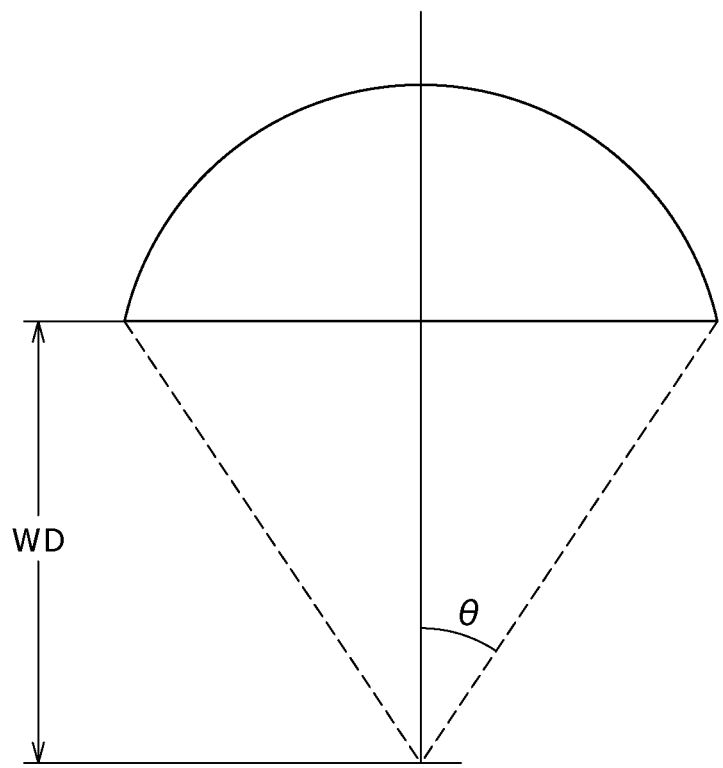
FIG. 16 is a diagrammatic view illustrating a performance of a lens.

Particularly, the positioning shape is preferably provided on both of the upper face and the lower face of a substrate as seen in FIG. 13 such that the positioning shape 56 provided on the upper face of the substrate is complementary in shape to a positioning shape 57 provided on the lower face of the substrate. Where the positioning shapes 56 and 57 are configured in this manner, when a plurality of such channel substrates 5b are stacked in the vertical direction as seen in FIG. 14, the channel substrates 5b are fitted with each other in the vertical direction, and consequently, transportation, storage and so forth of the channel substrates 5b can be carried out stably.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention is claimed as follows:

1. A channel substrate having a channel provided therein, comprising:
    a plurality of faces;
    a plurality of detection portions on one of said plurality of faces, said plurality of detection portions configured to detect a specimen in the channel using optical means, the plurality of detection portions having detection portion surfaces which have distances different from each other to the channel in a stepped configuration such that said detection portion surfaces are on different levels of said face;
    an introducing portion configured to introduce the specimen into the channel; and
    a discharging portion configured to discharge the specimen from the channel.

2. The channel substrate according to claim 1, wherein the detection portion surfaces of the plurality of detection portions have distances different from each other to the channel on opposite faces of the channel substrate.

3. The channel substrate according to claim 1, wherein two or more additional introducing portions are connected to the channel.

4. The channel substrate according to claim 1, further comprising:
   an identification shape from which information regarding the channel substrate can be identified.

5. The channel substrate according to claim 4, wherein the identification shape is a cutaway shape.

6. The channel substrate according to claim 1, further comprising
   a positioning shape provided on the channel substrate configured to define the position of the channel substrate upon installation of the channel substrate.

7. The channel substrate according to claim 6, wherein the positioning shape is provided on one of the faces of the channel substrate.

8. The channel substrate according to claim 6, wherein the faces include an upper face and a lower face and the positioning shape is provided on both of the upper and lower faces of the channel substrate such that the positioning shape provided on the upper face of the channel substrate is complementary to the positioning shape provided on the lower face of the channel substrate.

9. The channel substrate according to claim 1, wherein the specimen is selected from the group consisting of a particle, a plurality of particles and a fluid.

10. A channel substrate having a channel provided therein, comprising:
    a plurality of detection means on a face of said channel substrate for detecting a specimen in the channel using optical means, the plurality of detection means having detection portion surfaces which have distances different from each other to the channel in a stepped configuration such that said detection portion surfaces are on different levels of said face;
    introducing means for introducing the specimen into the channel; and
    discharging means for discharging the specimen from the channel.

11. The channel substrate according to claim 10, wherein the specimen is selected from the group consisting of a particle, a plurality of particles and a fluid.

* * * * *